United States Patent
Mori et al.

(10) Patent No.: US 9,908,957 B2
(45) Date of Patent: Mar. 6, 2018

(54) MODIFIED POLYVINYL ALCOHOL AND WATER-SOLUBLE FILM CONTAINING SAME

(71) Applicant: KURARAY CO., LTD., Kurashiki-shi (JP)

(72) Inventors: Yoko Mori, Osaka (JP); Masaki Kato, Kurashiki (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 15/108,174

(22) PCT Filed: Dec. 24, 2014

(86) PCT No.: PCT/JP2014/084179
§ 371 (c)(1),
(2) Date: Jun. 24, 2016

(87) PCT Pub. No.: WO2015/098979
PCT Pub. Date: Jul. 2, 2015

(65) Prior Publication Data
US 2016/0326285 A1 Nov. 10, 2016

(30) Foreign Application Priority Data
Dec. 25, 2013 (JP) .................. 2013-268119

(51) Int. Cl.
| C08F 216/06 | (2006.01) |
| C08F 218/08 | (2006.01) |
| C08F 8/12 | (2006.01) |
| C08J 5/18 | (2006.01) |
| A01N 25/30 | (2006.01) |
| C11D 3/37 | (2006.01) |
| C11D 17/04 | (2006.01) |

(52) U.S. Cl.
CPC ............ *C08F 216/06* (2013.01); *A01N 25/30* (2013.01); *C08F 8/12* (2013.01); *C08F 218/08* (2013.01); *C08J 5/18* (2013.01); *C11D 3/3753* (2013.01); *C11D 17/042* (2013.01); *C08F 2800/10* (2013.01); *C08J 2300/105* (2013.01); *C08J 2329/04* (2013.01)

(58) Field of Classification Search
None
See application file for complete search history.

(56) References Cited

U.S. PATENT DOCUMENTS

| 6,635,709 | B2* | 10/2003 | Kato ..................... C08F 2/20 525/386 |
| 7,928,166 | B2* | 4/2011 | Shibutani ................. C08F 8/12 139/420 A |
| 2002/0182348 | A1 | 12/2002 | Fujiwara et al. |
| 2004/0092635 | A1 | 5/2004 | Kitamura et al. |
| 2005/0113475 | A1* | 5/2005 | Nishida ..................... C08F 2/34 522/1 |
| 2011/0300387 | A1* | 12/2011 | Park ...................... C09J 129/04 428/414 |
| 2012/0164424 | A1 | 6/2012 | Vicari et al. |

FOREIGN PATENT DOCUMENTS

| JP | 4-71243 U | 6/1992 |
| JP | 4-164998 A | 6/1992 |
| JP | 4-170405 A | 6/1992 |
| JP | 6-340899 A | 12/1994 |
| JP | 2523951 Y2 | 1/1997 |
| JP | 9-272773 A | 10/1997 |
| JP | 10-60207 A | 3/1998 |
| JP | 2003-171424 A | 6/2003 |
| JP | 2004-161823 A | 6/2004 |
| JP | 2005-89655 A | 4/2005 |
| JP | 2005-139240 A | 6/2005 |
| JP | 2006-63242 A | 3/2006 |
| JP | 2006063242 A * | 3/2006 |
| JP | 2012-087821 A1 | 6/2012 |

OTHER PUBLICATIONS

Pasch, Advances in Polymer Science, 2000, 150, pp. 1-66.*
Lopez et al., Polymer Engineering and Science, 1999, 39(8), pp. 1346-1352.*
International Search Report dated Mar. 31, 2015 in PCT/JP14/084179 Filed Dec. 24, 2014.

* cited by examiner

*Primary Examiner* — Abigail Vanhorn
(74) *Attorney, Agent, or Firm* — Oblon, McClelland, Maier & Neustadt, L.L.P.

(57) ABSTRACT

Modified polyvinyl alcohol contains a monomer unit having a carboxyl group, wherein the modified polyvinyl alcohol has a degree of saponification of from 50 to 99.99 mol % and a viscosity-average degree of polymerization of from 200 to 5000 and satisfies formulae (1) to (3) below. The modified polyvinyl alcohol of the present invention thus obtained is particularly excellent in dispersibility in water.

$$0.8 \leq (Mw_{UV}/Mw_{RI}) \leq 1.2 \qquad (1)$$

$$2 \leq (Mw_{UV}/Mn_{UV}) \leq 8 \qquad (2)$$

$$0.01 \leq A_{280} \leq 0.8 \qquad (3)$$

6 Claims, No Drawings

MODIFIED POLYVINYL ALCOHOL AND WATER-SOLUBLE FILM CONTAINING SAME

TECHNICAL FIELD

The present invention relates to modified polyvinyl alcohol containing a monomer unit having a carboxyl group. The present invention also relates to a water-soluble film containing the modified polyvinyl alcohol. The present invention further relates to a package containing a chemical in the water-soluble film.

BACKGROUND ART

Polyvinyl alcohol (hereinafter, may be abbreviated as "PVA") is known as a water-soluble synthetic polymer. PVA is particularly excellent in strength and film forming properties compared with other synthetic polymers. PVA is therefore used as a material for film and fiber, an additive for paper and fiber processing, an adhesive, a stabilizer for emulsion polymerization and suspension polymerization, a binder for inorganics, and the like. PVA is thus heavily used in various applications.

In recent years, a method of using chemicals, such as household chemicals, like detergents, bleaches, and toiletries, agrochemicals, and industrial chemicals, by seal-packaging (unit packaging) in a water-soluble film in each unit amount has become popular. The method is described below. In advance, the content is seal-packaged (unit packaged) in a water-soluble film in each certain amount. For use, it is thrown into water remaining in the form of package. By dissolution of the water-soluble film, the content is dissolved or dispersed in water. The unit package is advantageous in that it allows use without directly touching hazardous chemicals in use, no measurement is required in use because the content is packaged in each certain amount, the container for packaging the chemical does not have to be disposed after use, and the like.

Since PVA films generally have advantages of being tough, excellent in transparency, and good in printability, they are often conventionally used as water-soluble films for unit package. In PVA, however, with a higher degree of saponification, the crystallinity increases and the ratio of crystal parts that are not dissolved in cold water increases. Therefore, for applications requiring cold water solubility, not PVA having a high degree of saponification, called a completely saponified type, but unmodified partially saponified PVA has been used. Water-soluble films using the unmodified partially saponified PVA have advantages of being readily dissolved in cold water and warm water, excellent in mechanical strength, and the like.

In recent years, from the perspective of workability, chemical resistance, environmental protection, and the like, there is a demand for a water-soluble film that simultaneously satisfies performance, such as having a faster rate of dissolution in cold water, being less easily broken by impact, having water solubility varied less with time during storage, and being good in biodegradability. Conventional unmodified partially saponified PVA films, however, have a problem that the cold water solubility decreases during storage for a long period. The water solubility is considered to decrease because the crystal gradually grows during storage. Moreover, when an alkaline or acidic substance is packaged in such unmodified partially saponified PVA film, saponification of acetate groups remaining in the partially saponified PVA occurs during the storage and crystallization proceeds to insolubilize the film. The required performance has thus not been obtained. In addition, when a chlorine containing compound, such as an agrochemical and an antiseptic, is packaged in a film using the unmodified partially saponified PVA to be left for a long period, the film is colored and cured and also the water solubility decreases with time to be insoluble or poorly soluble in water. The content is therefore not dissolved or dispersed in water in the state of remaining packaged in the film, and thus the original purpose is not achieved.

As a solution to such problems, a water-soluble film of modified PVA having an anionic group, such as a carboxyl group, is proposed. For example, Patent Document 1 discloses a water-soluble film of modified PVA having a monomer unit containing a carboxyl group, such as itaconic acid and maleic acid. Patent Document 2 discloses a water-soluble film of a composition containing modified PVA, having a monomer unit containing a carboxyl group and/or a sulfonic acid group, and polyhydric alcohol. Further, Patent Document 3 discloses water-soluble modified PVA with a monomer unit containing acrylic acid randomly introduced therein and a package using a film of the modified PVA.

Such water-soluble film of modified PVA having an anionic group, such as a carboxyl group, however, has a disadvantage of losing cold water solubility when making contact with an acidic substance. Further, the modified PVA is sometimes gelatinized by heat. In addition, the modified PVA is capable of increasing dissolubility in cold water by increasing the carboxyl group content while a water-soluble film thereof sometimes has reduced mechanical strength, so that it used not to be preferred. There is, accordingly, a demand for modified PVA that is excellent in dispersibility in water without gelation and the like and is further capable of obtaining a film excellent in cold water solubility and mechanical strength.

PRIOR ART DOCUMENTS

Patent Documents

Patent Document 1: JP 04-170405 A
Patent Document 2: JP 2005-139240 A
Patent Document 3: WO 2012/087821 A1

SUMMARY OF THE INVENTION

Problems to be Solved by the Invention

The present invention has been made to solve the above problems, and it is an object thereof to provide modified PVA that is excellent in dispersibility in water. It is also an object of the present invention to provide a water-soluble film that is excellent in cold water solubility and mechanical strength.

Means for Solving the Problems

As a result of intensive examinations to solve the problems, the present inventors found that carboxyl group-modified PVA that satisfies specific requirements particularly on an absorbance and molecular weight distribution is excellent in dispersibility in water and a water-soluble film containing the carboxyl group-modified PVA is excellent in cold water solubility and mechanical strength and thus have come to complete the present invention.

That is, the problems are solved by providing modified polyvinyl alcohol comprising a monomer unit having a carboxyl group, wherein the modified polyvinyl alcohol has a degree of saponification of from 50 to 99.99 mol % and a viscosity-average degree of polymerization of from 200 to 5000 and satisfies formulae (1) to (3) below.

$$0.8 \leq (Mw_{UV}/Mw_{RI}) \leq 1.2 \quad (1)$$

$$2 \leq (Mw_{UV}/Mn_{UV}) \leq 8 \quad (2)$$

$$0.01 \leq A_{280} \leq 0.8 \quad (3)$$

$Mw_{UV}$: weight-average molecular weight of the modified polyvinyl alcohol measured by an absorptiometer (measurement wavelength of 280 nm) in gel permeation chromatographic (hereinafter, may be abbreviated as GPC) measurement of the modified polyvinyl alcohol, $Mw_{RI}$: weight-average molecular weight of the modified polyvinyl alcohol measured by a differential refractive index detector in GPC measurement of the modified polyvinyl alcohol, $Mn_{UV}$: number-average molecular weight of the modified polyvinyl alcohol measured by an absorptiometer (measurement wavelength of 280 nm) in GPC measurement of the modified polyvinyl alcohol, $A_{280}$: absorbance (optical path length of 10 mm, wavelength of 280 nm) of a 1 mass % aqueous solution of the modified polyvinyl alcohol.

It is preferred that a content of the monomer unit is from 0.1 to 10 mol %.

A water-soluble film comprising the modified polyvinyl alcohol is a preferred embodiment of the present invention.

A package comprising a chemical contained in the water-soluble film is also another preferred embodiment of the present invention. It is preferred that the chemical is an agrochemical or a detergent.

Effects of the Invention

The carboxyl group-modified PVA of the present invention is particularly excellent in dispersibility in water. A water-soluble film containing the modified PVA is excellent in cold water solubility and mechanical strength. The water-soluble film of the present invention is accordingly used suitably as a packaging material for various chemicals, such as an agrochemical and a washing detergent.

MODES FOR CARRYING OUT THE INVENTION

[Carboxyl Group-Modified PVA]

The PVA of the present invention comprises a monomer unit having a carboxyl group, wherein the modified polyvinyl alcohol has a degree of saponification of from 50 to 99.99 mol % and a viscosity-average degree of polymerization of from 200 to 5000 and satisfies formulae (1) to (3) below.

$$0.8 \leq (Mw_{UV}/Mw_{RI}) \leq 1.2 \quad (1)$$

$$2 \leq (Mw_{UV}/Mn_{UV}) \leq 8 \quad (2)$$

$$0.01 \leq A_{280} \leq 0.8 \quad (3)$$

$Mw_{UV}$: weight-average molecular weight of the modified polyvinyl alcohol measured by an absorptiometer (measurement wavelength of 280 nm) in gel permeation chromatographic measurement of the modified polyvinyl alcohol, $Mw_{RI}$: weight-average molecular weight of the modified polyvinyl alcohol measured by a differential refractive index detector in gel permeation chromatographic measurement of the modified polyvinyl alcohol, $Mn_{UV}$: number-average molecular weight of the modified polyvinyl alcohol measured by an absorptiometer (measurement wavelength of 280 nm) in gel permeation chromatographic measurement of the modified polyvinyl alcohol, $A_{280}$: absorbance (optical path length of 10 mm, wavelength of 280 nm) of a 1 mass % aqueous solution of the modified polyvinyl alcohol.

The absorption of ultraviolet wavelength at 280 nm is derived from the structure of [—CO—(CH=CH—)$_2$].

Note that, in the GPC measurement,

Mobile phase: hexafluoroisopropanol with 20 mmol/l sodium trifluoroacetate (hereinafter, hexafluoroisopropanol may be abbreviated as HFIP), Sample injection volume: 100 μl of a 1.00 mg/ml solution Column temperature: 40° C.

Flow rate: 1 ml/min.

Cell Length of Absorptiometer: 10 mm.

In the present invention, GPC measurement is conducted using a GPC instrument equipped with a differential refractive index detector and an absorptiometer, the instrument allowing simultaneous measurement using these detectors. The absorptiometer has to allow measurement of an absorbance at a wavelength of 280 nm. A cell in a detection unit in the absorptiometer is used that has a cell length (optical path length) of 10 mm. The absorptiometer may be a type which measures absorption of ultraviolet light at a specific wavelength or a type which spectrometrically measures absorption of ultraviolet light at a wavelength in a specific range. Signal intensity measured by a differential refractive index detector is proportional to a concentration (mg/ml) of the modified PVA. In contrast, an absorptiometer detects only the modified PVA which have adsorption at a predetermined wavelength. For each molecular-weight component in the modified PVA, a concentration and an absorbance at a predetermined wavelength can be measured by the GPC measurement described above.

As a solvent and a mobile phase used for dissolution of the modified PVA measured in the above GPC measurement, HFIP with 20 mmol/L sodium trifluoroacetate is used. HFIP can dissolve the modified PVA and methyl polymethacrylate (hereinafter, may be abbreviated as "PMMA"). Furthermore, addition of sodium trifluoroacetate allows inhibition of adsorption of the modified PVA to a column filler. In the GPC measurement, the flow rate is 1 ml/min. and the column temperature is 40° C. A GPC column used in the GPC measurement is not particularly limited as long as it is capable of separating the modified PVA of the present invention according to the molecular weight. Specifically, "GPC HFIP-806M" manufactured by Showa Denko K. K. or the like is suitably used.

In the GPC measurement, monodisperse PMMA is used as a standard. Several types of standard PMMA with a different molecular weight are measured to form a calibration curve from GPC elution volumes and molecular weights of the standard PMMA. In the present invention, for measurement by a differential refractive index detector, a calibration curve formed using the detector is used, while for measurement by an absorptiometer, a calibration curve formed using the detector is used. Using these calibration curves, a GPC elution volume is converted to a molecular weight of the modified PVA.

The modified PVA of the present invention is dissolved in the above solvent to prepare a measurement sample. A concentration of the modified PVA as the measurement sample is 1.00 mg/ml and an injection volume is 100 µl. Note that, if a viscosity degree of polymerization of the modified PVA exceeds 2400, an excluded volume is so increased that measurement at a concentration of the modified PVA of 1.00 mg/ml is sometimes not reproducible. In such a case, an appropriately diluted sample (injection volume of 100 µl) is used.

$Mw_{UV}$ and $Mn_{UV}$ are obtained from the chromatogram of a plot of a value measured by an absorptiometer (280 nm) to a molecular weight of the modified PVA converted from GPC elution volumes. $Mw_{RI}$ is obtained from the chromatogram of a plot of a value measured by a differential refractive index detector to a molecular weight of the modified PVA converted from GPC elution volumes. In the present invention, $Mw_{UV}$, $Mw_{RI}$, and $Mn_{UV}$ are values in PMMA equivalent.

The modified PVA of the present invention satisfies the formula (1) below.

$$0.8 \leq (Mw_{UV}/Mw_{RI}) \leq 1.2 \quad (1)$$

When $(Mw_{UV}/Mw_{RI})$ is less than 0.8, dispersibility of the modified PVA in water and cold water solubility of the water-soluble film thus obtained become insufficient. $(Mw_{UV}/Mw_{RI})$ is preferably 0.82 or more, more preferably 0.84 or more, and even more preferably 0.86 or more. In contrast, when $(Mw_{UV}/Mw_{RI})$ exceeds 1.2, dispersibility of the modified PVA in water and mechanical strength of the water-soluble film thus obtained become insufficient. $(MW_{UV}/MW_{RI})$ is preferably 1.15 or less, more preferably 1.1 or less, even more preferably 1.05 or less, and particularly preferably 0.99 or less. The calculated values of $Mw_{UV}$ and $Mw_{RI}$ being equivalent values in such a manner are considered because monomer units having carboxyl groups are introduced uniformly and randomly in the modified PVA.

$Mw_{RI}$ is a weight-average molecular weight of the modified PVA, and $Mw_{UV}$ is a weight-average molecular weight of the components constituted to absorb ultraviolet rays at a wavelength of 280 nm contained in the modified PVA. Accordingly, when $(Mw_{UV}/Mw_{RI})$ is 0.99 or less, low molecular weight components in the modified PVA contain many components absorbing ultraviolet rays at a wavelength of 280 nm. It is possible to obtain the modified PVA having $(Mw_{UV}/Mw_{RI})$ of 0.99 or less by, for example, employing a polymerization method described later.

The PVA of the present invention satisfies the formula (2) below.

$$2 \leq (Mw_{UV}/Mn_{UV}) \leq 8 \quad (2)$$

When $(Mw_{UV}/Mn_{UV})$ is less than 2, it is indicated that the ratio of low molecular weight components is low in the components constituted to absorb a wavelength of 280 nm in the modified PVA. It is difficult to manufacture the modified PVA with $(Mw_{UV}/Mn_{UV})$ of less than 2. $(Mw_{UV}/Mn_{UV})$ is preferably 2.2 or more, more preferably 2.4 or more, and even more preferably 2.6 or more. In contrast, when $(Mw_{UV}/Mn_{UV})$ exceeds 8, it is indicated that the ratio of low molecular weight components is high in the components constituted to absorb a wavelength of 280 nm in the modified PVA. When $(Mw_{UV}/Mn_{UV})$ exceeds 8, dispersibility of the modified PVA in water and mechanical strength of the film thus obtained become insufficient. $(Mw_{UV}/Mn_{UV})$ is preferably 7 or less, more preferably 6 or less, even more preferably 4 or less, and particularly preferably 3.2 or less.

$Mn_{UV}$ is a number-average molecular weight of components constituted to absorb ultraviolet rays at a wavelength of 280 nm contained in the modified PVA, and $Mw_{UV}$ is a weight-average molecular weight of the components constituted to absorb ultraviolet rays at a wavelength of 280 nm contained in the modified PVA. Generally, $Mn_{UV}$ is an average molecular weight strongly influenced by low molecular weight components and $Mw_{UV}$ is an average molecular weight strongly influenced by high molecular weight components, so that $(Mw_{UV}/Mn_{UV})$ is used as an index of molecular weight distribution of polymers. Accordingly, when $(Mw_{UV}/Mn_{UV})$ is low, molecular weight distribution of the components to absorb ultraviolet rays at a wavelength of 280 nm in the modified PVA is narrow. The modified PVA with low $(Mw_{UV}/Mn_{UV})$ is obtained by, for example, employing a polymerization method described later.

For measurement of the absorbance $A_{280}$, a cell with an optical path length of 10 mm is used. The measurement wavelength is 280 nm. The modified PVA (film) is dissolved in distilled water to prepare a 0.1 mass % aqueous solution, served for the measurement.

The PVA of the present invention satisfies the formula (3) below.

$$0.01 \leq A_{280} \leq 0.8 \quad (3)$$

When the absorbance of $A_{280}$ is less than 0.01, cold water solubility of the water-soluble film thus obtained becomes insufficient. The absorbance of $A_{280}$ is preferably 0.02 or more and more preferably 0.03 or more. In contrast, when the absorbance of $A_{280}$ exceeds 0.8, dispersibility of the modified PVA in water and mechanical strength of the water-soluble film thus obtained become insufficient. The absorbance $A_{280}$ is preferably 0.7 or less and more preferably 0.6 or less.

The viscosity-average degree of polymerization of the modified PVA of the present invention is measured in accordance with JIS-K6726. That is, the modified PVA is resaponified to a degree of saponification of 99.5 mol % or more and refined, followed by measuring limiting viscosity [η] (liter/g) in water at 30° C. to be used in the following equation for the degree.

$$P = ([\eta] \times 10000/8.29)^{(1/0.62)}$$

The modified PVA of the present invention has a viscosity-average degree of polymerization of from 200 to 5000. When the viscosity-average degree of polymerization is less than 200, practical strength is not obtained. Accordingly, mechanical strength of the water-soluble film containing the modified PVA becomes insufficient. The viscosity-average degree of polymerization is preferably 250 or more, more preferably 300 or more, and even more preferably 400 or more. In contrast, when the viscosity degree of polymerization exceeds 5000, the viscosity of the aqueous solution of the modified PVA dissolved therein becomes excessively high and thus it is difficult to be handled. The viscosity-average degree of polymerization is preferably 4500 or less, more preferably 4000 or less, and even more preferably 3500 or less.

The degree of saponification of the modified PVA is measured in accordance with JIS-K6726. The modified PVA has a degree of saponification of from 50 to 99.99 mol %. When the degree of saponification is less than 50 mol %, the water solubility of the modified PVA severely decreases. The degree of saponification is preferably 70 mol % or more and more preferably 80 mol % or more. In contrast, when the degree of saponification exceeds 99.99 mol %, it is not possible to stably produce the modified PVA and dispersibility in water becomes insufficient. The degree of saponification is preferably 99.7 mol % or less and more preferably 99.6 mol % or less.

The monomer having a carboxyl group in the present invention may be a monomer copolymerizable with a vinyl ester monomer and having carboxylic acid or salt thereof existing in the PVA after saponification. Specifically, maleic acid or salt thereof, esters of maleic acid, such as monomethyl maleate, dimethyl maleate, monoethyl maleate, and diethyl maleate; itaconic acid (IA) or salt thereof, esters of itaconic acid, such as monomethyl itaconate, dimethyl itaconate, monoethyl itaconate, and diethyl itaconate; fumaric acid or salt thereof, esters of fumaric acid, such as monomethyl fumarate, dimethyl fumarate, monoethyl fumarate, and diethyl fumarate; maleic anhydride, itaconic anhydride, or a derivative thereof; acrylic acid or salt thereof, esters of acrylic acid, such as methyl acrylate, ethyl acrylate, n-propyl acrylate, and isopropyl acrylate; and methacrylic acid or salt thereof, esters of methacrylic acid, such as methyl methacrylate, ethyl methacrylate, n-propyl methacrylate, and isopropyl methacrylate are suitably used. Among them, from the perspective of cold water solubility of a film formed of the monomer, maleic acid, monomethyl maleate (MMM), dimethyl maleate, itaconic acid, monomethyl itaconate, dimethyl itaconate, acrylic acid, methyl acrylate (MA), methacrylic acid, methyl methacrylate are preferred. Such monomer having a carboxyl group may be used singly or in combination of two or more.

The content of the monomer unit having a carboxyl group is preferably from 0.1 to 10 mol %, more preferably from 0.5 to 8.0 mol %, and even more preferably from 1.0 to 5.0 mol %. The content of the monomer unit being in the above range even more improves the dispersibility in water and the cold water solubility and the mechanical strength of the water-soluble film thus obtained. The content means content of the monomer units having carboxyl groups relative to the total monomer units in the carboxyl group-modified PVA.

The modified PVA of the present invention may be a blend containing modified PVA and unmodified PVA. In this case, the blend should have averages of viscosity-average degrees of polymerization, degrees of saponification, ultraviolet absorption, and molecular weight distributions in the above ranges.

[Method of Producing Modified PVA]

A method of producing the modified PVA of the present invention is described below in detail. The present invention is not limited to the embodiments described below.

The modified PVA of the present invention is produced by, for example, copolymerizing a vinyl ester monomer and a monomer having a carboxyl group to obtain a vinyl ester copolymer, followed by saponification thereof using an alkaline or acid catalyst in an alcohol solution.

Examples of the vinyl ester monomer may include vinyl formate, vinyl acetate, vinyl propionate, vinyl valerate, vinyl caprate, vinyl laurate, vinyl stearate, vinyl benzoate, vinyl pivalate, vinyl versatate, and the like, and particularly from the perspective of costs, vinyl acetate is preferred.

Examples of the method of copolymerizing a vinyl ester monomer and a monomer having a carboxyl group in the molecule may include known methods, such as bulk polymerization, solution polymerization, suspension polymerization, and emulsion polymerization. Among these methods, bulk polymerization performed without solvent or solution polymerization using a solvent, such as alcohol, is normally employed. To enhance the effects of the present invention, solution polymerization to polymerize with lower alcohol is preferred. Although not particularly limited, the lower alcohol is preferably alcohol having a carbon number of 3 or less, such as methanol, ethanol, propanol, and isopropanol, and normally methanol is used.

Examples of the initiator used for the polymerization reaction may include known initiators, without impairing the effects of the present invention, such as azo-based initiators like 2,2'-azobisisobutyronitrile, 2,2'-azobis(2,4-dimethylvaleronitrile), and 2,2'-azobis(4-methoxy-2,4-dimethylvaleronitrile); and organic peroxide initiators like benzoyl peroxide and n-propyl peroxycarbonate.

To obtain the modified PVA of the present invention, the modified vinyl ester copolymer is obtained by a two-vessel continuous polymerization method. The method is described below. For the polymerization, a polymerizer provided with a first polymerization vessel and a second polymerization vessel is used. To the first polymerization vessel, a vinyl ester monomer, a monomer having a carboxyl group, an initiator, and a solvent are fed continuously.

A mass ratio (monomer having a carboxyl group/vinyl ester monomer) of an amount of the fed monomer having a carboxyl group to an amount of the fed vinyl ester monomer is preferably from 0.00001 to 0.009. A mass ratio (initiator/vinyl ester monomer) of an amount of the fed initiator to an amount of the fed vinyl ester monomer is preferably from 0.000001 to 0.001. A mass ratio (solvent/vinyl ester monomer)) of an amount of the fed solvent to an amount of the fed vinyl ester monomer is preferably from 0.1 to 0.4.

Average residence time of the components fed to the first polymerization vessel in the first polymerization vessel is preferably from 30 to 150 minutes. A reaction temperature in the first polymerization vessel is preferably from 55 to 85° C. and even more preferably from 60 to 80° C. A rate of polymerization of the monomers in a polymerization liquid taken out of the first polymerization vessel is preferably from 5 to 50%.

The polymerization liquid is continuously taken out of the first polymerization vessel to be fed to the second polymerization vessel. At this point, the monomer having a carboxyl group and the initiator are further fed continuously to the second polymerization vessel. A ratio (monomer having a carboxyl group/vinyl ester monomer) of the mass of the monomer having a carboxyl group fed to the second polymerization vessel to the mass of the vinyl ester monomer fed to the first polymerization vessel is preferably from 0.00001 to 0.009. A ratio (initiator/vinyl ester monomer) of the mass of the initiator fed to the second polymerization vessel to the mass of the vinyl ester monomer fed to the first polymerization vessel is preferably from 0.000001 to 0.001. By feeding the initiator not only to the first polymerization vessel but also to the second polymerization vessel in such a manner, it is possible to obtain the modified PVA of the present invention.

By saponifying the vinyl ester copolymer obtained by the two-vessel continuous polymerization method, modified PVA with low ($Mw_{UV}/Mw_{RI}$) can be obtained. Although not yet fully clarified, the principle to obtain such modified PVA is considered as follows. In the above polymerization method, radicals derived from the initiator are fed by adding the initiator also to the second polymerization vessel. As a result, vinyl ester-based copolymers of a low molecular weight increase. Further, in the second polymerization vessel, a chain transfer reaction to acetaldehyde produced by decomposition of the vinyl ester monomers in the first polymerization vessel occurs, and a terminal methyl ketone structure is generated in the vinyl ester-based copolymers of a low molecular weight. Then, a polyene structure with chain double bonds in a molecular end is produced by subsequent heat treatment, such as drying. Due to such reaction mechanism, it is considered that more modified PVA, compared with the past, of a low molecular weight having a polyene structure that absorbs ultraviolet rays at a wavelength of 280 nm is obtained.

Average residence time of the components fed from the first polymerization vessel to the second polymerization vessel and the components added to the second polymerization vessel in the second polymerization vessel is preferably from 30 to 150 minutes. A reaction temperature in the second polymerization vessel is preferably from 55 to 85° C. and even more preferably from 60 to 80° C. A rate of polymerization of the monomers in a polymerization liquid taken out of the second polymerization vessel is preferably from 10 to 80%.

By saponifying the vinyl ester copolymer thus obtained in an alcohol solvent, it is possible to obtain the modified PVA of the present invention.

As a catalyst for the saponification reaction of the vinyl ester-based copolymer, an alkaline material is normally used, and examples of it may include hydroxides of alkali metal, such as potassium hydroxide and sodium hydroxide, and alkali metal alkoxides, such as sodium methoxide. An amount of the alkaline material used is preferably from 0.002 to 0.2 in a molar ratio to the vinyl ester monomer units of the vinyl ester copolymer and particularly preferably from 0.004 to 0.1. The saponification catalyst may be added collectively at an initial stage of the saponification reaction, or may be added partially at an initial stage of the saponification reaction and the rest may be additionally added during the saponification reaction.

Examples of the solvent that can be used for the saponification reaction may include methanol, methyl acetate, dimethyl sulfoxide, diethyl sulfoxide, dimethyl formamide, and the like. Among these solvents, methanol is used preferably. At this point, a water content of the methanol is regulated preferably from 0.001 to 1 mass %, more preferably from 0.003 to 0.9 mass %, and particularly preferably from 0.005 to 0.8 mass %.

The saponification reaction is performed at a temperature of preferably from 5 to 80° C. and more preferably from 20 to 70° C. The saponification reaction is performed preferably from 5 minutes to 10 hours and more preferably from 10 minutes to 5 hours. The saponification reaction may be performed in either method of the batch method or the continuous method.

After finishing the saponification reaction, the remained catalyst may be neutralized as needed. Examples of the usable neutralizer may include organic acid, such as acetic acid and lactic acid, ester compounds, such as methyl acetate, and the like. After the saponification reaction or after the neutralization reaction, by washing and drying as needed, it is possible to obtain the modified PVA of the present invention.

Examples of another method to obtain the modified PVA of the present invention may include a method of obtaining the modified PVA by mixing a vinyl ester-based copolymer of a low molecular weight containing a monomer unit having a carboxyl group and an unmodified vinyl ester-based polymer of a high molecular weight and subsequent saponification as described above. Further, the examples may include a method comprising mixing modified PVA of a low molecular weight containing a monomer unit having a carboxyl group and unmodified PVA of a high molecular weight.

The modified PVA of the present invention is excellent in dispersibility without gelation and the like when put into an aqueous solution. Then, a water-soluble film containing the modified PVA of the present invention is excellent in cold water solubility and mechanical strength.

[Water-Soluble Film]

The present invention is a water-soluble film containing the above modified PVA. Although even the water-soluble film only of the modified PVA sufficiently exhibits the performance, known plasticizers, defoaming agents, slip agents, antiblocking agents, and the like may be added as needed. The content of such additive is normally 20 mass % or less and preferably 10 mass % or less. The modified PVA content in the water-soluble film is normally 50 mass % or more, more preferably 80 mass % or more, and even more preferably 90 mass % or more.

The water-soluble film of the present invention may contain, without inhibiting the effects of the present invention, regular PVA and other modified PVA; water-soluble or water-dispersible resins, such as polyacrylic acid or salt thereof, polyacrylamide, starch, and cellulose; water-based emulsions and water-based suspensions; and thermoplastic resins other than PVA, such as polyolefin like polyethylene and polypropylene, nylon, polyester, polyvinyl chloride, polystyrene, polyvinyl butyral, and an ethylene-vinyl acetate copolymer or a saponification product thereof. In the water-soluble film of the present invention, the content of resin other than PVA containing a monomer unit having a carboxyl group is normally 50 mass % or less, preferably 20 mass % or less, and more preferably 10 mass % or less.

A method of producing the water-soluble film of the present invention is not particularly limited, and it is possible to produce the film by known methods, such as a casting method and a melt extrusion method. For example, the film can be produced in the following method. The modified PVA is dissolved in a water-based solvent. At this point, the above additives may be added as needed. The solution thus obtained is casted on a smooth plate or roll and dried to obtain a water-soluble film. The water-soluble film thus obtained is transparent and uniform. The water-based solvent is preferably water. The material for the plate and the roll is not particularly limited as long as it is smooth and rigid, and examples of the material may include steel, aluminum, glass, a resin (e.g., polyolefin, polyethylene, polyamide, polyvinyl chloride, polycarbonate, polyhalocarbon, etc.), and the like. Examples of the drying method may include a method of drying by heating a plate or a film used for casting, a method of hot air drying, a method of drying by radiating infrared rays, and the like. As a specific method of producing the film, a modified PVA solution is casted by a standard (drum type) industrial film casting machine for film production, followed by drying in an oven to obtain a water-soluble film.

Although the thickness of the water-soluble film of the present invention is not particularly limited, it is preferably from 10 to 200 μm. The film shape may be smooth, whereas it is available to provide unevenness to the film by embossing and the like. Unevenness of the film is effective from the perspective of cold water solubility.

In addition, the water-soluble film of the present invention may be laminated with other PVA films, films of other water-soluble resins, such as starch and cellulose, biodegradable films, paper, nonwoven fabric, and the like.

The water-soluble film of the present invention has a good surface appearance as a packaging material and is excellent in cold water solubility and mechanical strength. Accordingly, a package having a chemical packaging in the water-soluble film is also another preferred embodiment of the present invention. Examples of the type of chemical may include an agrochemical, a detergent, and the like. The physical properties of the chemical are not particularly limited and may be any of acid, neutral, and alkaline. The form of chemical may be any of liquid, powder, granules, and lamp. Although not particularly limited, the form of package is preferably the form of unit package to package (preferably seal-package) a chemical in each unit amount.

EXAMPLES

The present invention is described below even more specifically with reference to Examples. In Examples and Comparative Examples below, "parts" and "%" are on a mass basis unless otherwise specified. A "degree of polymerization" means a "viscosity-average degree of polymerization".

[Degree of Polymerization and Degree of Saponification of Modified PVA]

The degree of polymerization and the degree of saponification of the carboxyl group-modified PVA were measured by the method of JIS-K6726 (1994).

[GPC Measurement of Modified PVA]

(Measuring Device)

GPC measurement was performed using "GPC max" manufactured by VISCOTECH Co., Ltd. As a differential refractive index detector, "TDA 305" manufactured by VISCOTECH Co., Ltd. was used. As an ultraviolet-visible absorptiometer, "UV Detector 2600" manufactured by VISCOTECH Co., Ltd. was used. An optical path length of a detection cell in the absorptiometer was 10 mm. For a GPC column, "GPC HFIP-806M" from Showa Denko K.K. was used. For analysis software, OmniSEC (Version 4.7.0.406) attached to the device was used.

(Measurement Conditions)

Carboxyl group-modified PVA was dissolved in hexafluoroisopropanol (hereinafter, abbreviated as "HFIP") containing 20 millimole/liter of sodium trifluoroacetate to prepare a 1.00 mg/ml solution. For measurement, the solution filtered through a 0.45 μm filter made of polytetrafluoroethylene was used. For a mobile phase, one same as the HFIP containing sodium trifluoroacetate with PVA dissolved therein was used, and the flow rate was 1.0 ml/min. The injection volume was 100 μl and the column temperature was at 40° C. for measurement.

For a sample with a degree of polymerization of PVA exceeding 2400, an appropriately diluted sample (100 μl) was used for GPC measurement.

(Preparation of Calibration Curve)

Methyl polymethacrylate (hereinafter, abbreviated as "PMMA") (peak-top molecular weight: 1944000, 790000, 467400, 271400, 144000, 79250, 35300, 13300, 7100, 1960, 1020, 690) produced by Agilent Technologies was measured as standards, and in the analysis software, a calibration curve to convert an elution volume to a PMMA molecular weight was formed for analysis, respectively for the differential refractive index detector and the absorptiometer. For the preparation of each calibration curve, the above analysis software was used. In measurement of methyl polymethacrylate in this measurement, a column capable of separating the peaks of standard samples with a molecular weight of 1944000 and 271400, respectively, was used.

In the above conditions, GPC measurement of the PVA obtained in Examples and Comparative Examples below was performed. Measurement by the absorptiometer (measurement wavelength of 280 nm) and measurement by the differential refractive index detector were performed simultaneously. From the chromatogram of a plot of values measured by the absorptiometer (measurement wavelength of 280 nm) to a molecular weight of the modified PVA converted from the GPC elution volumes, a weight-average molecular weight $Mw_{UV}$ and a number-average molecular weight $Mn_{UV}$ of the modified PVA were obtained. From the chromatogram of a plot of values measured by the differential refractive index detector to a molecular weight of the modified PVA converted from the GPC elution volumes, a weight-average molecular weight $Mw_{RI}$ of the modified PVA was obtained.

[Absorbance Measurement of Aqueous Solution of Modified PVA]

(Measuring Device)

Absorbance measurement was performed using an absorptiometer "UV-2450" manufactured by Shimadzu Corp. The PVA obtained in Examples and Comparative Examples below was dissolved in distilled water to prepare a 0.1 mass % aqueous solution. Then, the aqueous solution was put into a cell (optical path length of 10 mm) to measure the absorbance at a wavelength of 280 nm using the absorptiometer.

[Synthesis of Polyvinyl Acetate]

PVAc-1

Facilities were used in which a glass polymerization vessel (first polymerization vessel) with a vessel volume of 5 liters provided with a reflux condenser, a material feed line, a thermometer, a nitrogen inlet, and an impeller and a glass polymerization vessel (second polymerization vessel) with a vessel volume of 5 liters provided with a reflux condenser, a material feed line, a thermometer, a nitrogen inlet, and an impeller were connected in series via a metering pump. To the first polymerization vessel, vinyl acetate (VAM) (2.19 L/H), methanol (0.41 L/H), a 20% methanol solution (0.10 L/H) of monomethyl maleate (MMM), and a 2% methanol solution (0.03 L/H) of 2,2'-azobis(4-methoxy-2,4-dimethoxyvaleronitrile) (AMV) were continuously fed using the metering pump. The polymerization liquid was continuously taken out of the first polymerization vessel to be fed to the second polymerization vessel in such a manner that a liquid level in the first polymerization vessel became constant. To the second polymerization vessel, a 20% methanol solution of MMM (0.06 L/H) and a 2% methanol solution of AMV (0.02 L/H) were continuously fed using the metering pump. The polymerization liquid was continuously taken out of the second polymerization vessel in such a manner that a liquid level in the polymerization vessel became constant. Regulation was performed to have a rate of polymerization of vinyl acetate in the polymerization liquid taken out of the first polymerization vessel of 20.0% and to have a rate of polymerization of vinyl acetate in the polymerization liquid taken out of the second polymerization vessel of 40%. Residence time in the first polymerization vessel was 2 hours, and residence time in the second polymerization vessel was 2 hours. The temperature of the polymerization liquid taken out of the first polymerization vessel was at 63° C., and the temperature of the polymerization liquid taken out of the second polymerization vessel was at 63° C. By taking the polymerization liquid out of the second polymerization vessel to introduce methanol vapor to the polymerization liquid, unreacted vinyl acetate was removed to obtain a methanol solution of polyvinyl acetate (PVAc-1) (concentration of 35%).

PVAc-2 to 20

In the same manner as the above PVAc-1 other than changing into the conditions indicated in Table 1, respective PVAc-2 to 20 were synthesized.

TABLE 1

| | First Polymerization Vessel | | | | | | Second Polymerization Vessel | | | |
|---|---|---|---|---|---|---|---|---|---|---|
| Synthesis Example | VAM (L/H) | MeOH (L/H) | AMV (L/H) | Monomer Having Carboxyl Group Type | Monomer Having Carboxyl Group (L/H) | Rate of Polymerization (%) | Residence Time (h) | AMV (L/H) | Monomer Having Carboxyl Group Type | Monomer Having Carboxyl Group (L/H) | Rate of Polymerization (%) | Residence Time (h) |
| PVAc-1 | 2.19 | 0.41 | 0.03 | MMM | 0.10 | 20 | 2 | 0.02 | MMM | 0.06 | 40 | 2 |
| PVAc-2 | 2.19 | 0.41 | 0.03 | MMM | 0.10 | 23 | 2 | 0.01 | MMM | 0.06 | 38 | 2 |
| PVAc-3 | 2.19 | 0.58 | 0.03 | IA | 0.04 | 20 | 2 | 0.02 | IA | 0.03 | 40 | 2 |
| PVAc-4 | 1.75 | 0.35 | 0.04 | MA | 0.13 | 25 | 2 | 0.05 | MA | 0.12 | 50 | 2 |
| PVAc-5 | 2.58 | 0.11 | 0.02 | MMM | 0.45 | 17 | 2 | 0.01 | MMM | 0.27 | 34 | 2 |
| PVAc-6 | 2.19 | 0.56 | 0.03 | MMM | 0.01 | 20 | 2 | 0.02 | MMM | 0.01 | 40 | 2 |
| PVAc-7 | 3.65 | 0.70 | 0.01 | MMM | 0.24 | 12 | 2 | 0.01 | MMM | 0.12 | 24 | 2 |
| PVAc-8 | 2.19 | 1.07 | 0.04 | — | — | 20 | 2 | 0.02 | — | — | 40 | 2 |
| PVAc-9 | 2.43 | 0.60 | 0.03 | — | — | 18 | 2 | 0.01 | — | — | 36 | 2 |
| PVAc-10 | 1.99 | 0.43 | 0.04 | MMM | 0.18 | 22 | 2 | 0.03 | MMM | 0.12 | 44 | 2 |
| PVAc-11 | 3.65 | 0.11 | 0.01 | MMM | 0.12 | 12 | 2 | 0.01 | MMM | 0.06 | 24 | 2 |
| PVAc-12 | 1.46 | 0.89 | 0.08 | MMM | 0.09 | 30 | 2 | 0.04 | MMM | 0.06 | 60 | 2 |
| PVAc-13 | 2.19 | 0.61 | 0.03 | — | — | 20 | 2 | 0.02 | — | — | 40 | 2 |
| PVAc-14 | 2.92 | 0.31 | 0.02 | MMM | 0.22 | 15 | 2 | 0.01 | MMM | 0.12 | 30 | 2 |
| PVAc-15 | 2.19 | 0.97 | 0.03 | — | — | 20 | 2 | 0.02 | — | — | 40 | 2 |
| PVAc-16 | 2.43 | 0.52 | 0.03 | — | — | 18 | 2 | 0.01 | — | — | 36 | 2 |
| PVAc-17 | 1.90 | 0.44 | 0.04 | MMM | 0.18 | 23 | 2 | 0.04 | MMM | 0.12 | 46 | 2 |
| PVAc-18 | 4.87 | 0.05 | 0.01 | MMM | 0.14 | 9 | 2 | 0.01 | MMM | 0.06 | 18 | 2 |
| PVAc-19 | 1.25 | 1.01 | 0.12 | MMM | 0.08 | 35 | 2 | 0.06 | MMM | 0.06 | 70 | 2 |
| PVAc-20 | 3.34 | 0.63 | 0.05 | MMM | 0.15 | 20 | 2 | 0.00 | MMM | 0.06 | 26 | 2 |

1) MMM: monomethyl maleate
IA: itaconic acid
MA: methyl acrylate

Example 1

To 771.4 parts of a methanol solution of polyvinyl acetate (the above polymer in the solution is 200.0 parts) prepared by further adding methanol to a methanol solution of the polyvinyl acetate (PVAc-1) (concentration of 35%), 27.9 parts of a 10% methanol solution of sodium hydroxide was added for saponification at 40° C. (concentration of the above polymer in the saponification solution was 25%, molar ratio of sodium hydroxide to the vinyl acetate unit in the above polymer was 0.008). A gelatinous substance was produced approximately 15 minutes after adding the methanol solution of sodium hydroxide, and it was ground by a grinder and further left at 40° C. for 1 hour. The saponification thus proceeded, followed by adding 500 parts of methyl acetate to neutralize the remaining alkali. After confirming finish of the neutralization using a phenolphthalein indicator, the mixture was filtered to obtain a white solid. To the white solid, 2,000 parts of methanol were added and left at room temperature for 3 hours and then washed. The washing operation was repeated three times, followed by centrifugal deliquoring to obtain a white solid. The white solid thus obtained was dried in a drier at 105° C. for 3 hours to obtain PVA. The degree of polymerization was 1800, the degree of saponification was 93 mol %, and the content of the monomer unit having a carboxyl group was 2.0 mol %. The content of the monomer unit having a carboxyl group was obtained by analyzing the modified PVAc before saponification using $^1$H-NMR at 500 MHz (solvent: CDCl$_3$). Table 2 indicates values of the above formulae (1) to (3). The physical properties of the modified PVA thus obtained were evaluated in the following method. Table 2 indicates the evaluation results.

[Dispersibility of Modified PVA in Water]

A beaker containing 90 g of water was stirred at 200 rpm and 10 g of the modified PVA obtained in Example 1 was gradually added thereto. The state of aggregation of the modified PVA was visually observed to be evaluated based on the following criteria.

A: Dissolved, or completely dispersed
B: Slightly aggregated
C: Not at all dispersed and severely aggregated

[Cold Water Solubility of Water-Soluble Film]

Using an 8% aqueous solution of the modified PVA obtained in Example 1, a film was formed by a drum film forming apparatus to form a film having a thickness of 32 µm. The film was subjected to humidity control at 20° C., 65% RH, and the film was sandwiched between two 3×3 cm frames for fixation. The film was immersed in distilled water at 20° C. and stirred at 400 rpm, and time to completely dissolve the film was measured to be evaluated based on the following criteria.

A: Less than 20 seconds
B: Not less than 20 seconds and less than 100 seconds
C: 100 seconds or more

[Mechanical Strength of Water-Soluble Film]

The film formed as above was cut in a width of 1 cm and subjected to strength-elongation measurement at 20° C., 65% RH using AG-IS manufactured by Shimadzu Corp. in the conditions of a distance between chucks of 50 mm and a tensile speed of 500 mm/min. to obtain toughness to break from the stress-strain curve. Each sample was measured five times and an average value of the measurements was calculated to be evaluated based on the following criteria.

A: 280 kgf/mm or more
B: Not less than 240 kgf/mm and less than 280 kgf/mm
C: Less than 240 kgf/mm Examples 2 to 9, Comparative Examples 1 to 5

In the same manner as the Example 1 other than changing into the conditions indicated in Table 2, each PVA was synthesized to form a water-soluble film using the PVA. Table 2 indicates data on the physical properties of the PVA thus obtained. GPC measurement and absorbance measurement were performed in the same manner as in Example 1. The results are indicated in Table 2. The PVA and the water-soluble film thus obtained were subjected to evaluation of dispersibility in water, cold water solubility, and mechanical strength in the same manner as in Example 1. The results are indicated in Table 2.

TABLE 2

|  | PVAc[1] | Saponification | | Degree of Polymerization | Degree of Saponification (mol %) | Monomer Unit Having Carboxyl Group | |
|---|---|---|---|---|---|---|---|
|  |  | PVAc (%) | NaOH (molar ratio) |  |  | Type[2] | Content (mol %) |
| Example 1 | PVAc-1 | 25 | 0.008 | 1800 | 93 | MMM | 2.0 |
| Example 2 | PVAc-2 | 25 | 0.008 | 1800 | 93 | MMM | 2.0 |
| Example 3 | PVAc-3 | 25 | 0.006 | 1700 | 85 | IA | 1.0 |
| Example 4 | PVAc-4 | 25 | 0.02 | 1300 | 94.5 | MA | 5.0 |
| Example 5 | PVAc-5 | 25 | 0.01 | 1800 | 93 | MMM | 8.0 |
| Example 6 | PVAc-6 | 25 | 0.007 | 1800 | 93 | MMM | 0.2 |
| Example 7 | PVAc-7(50) PVAc-8(50) | 25 | 0.008 | 1800 | 93 | MMM | 2.0 |
| Example 8 | PVAc-9(50) PVAc-10(50) | 25 | 0.008 | 1800 | 93 | MMM | 2.0 |
| Example 9 | PVAc-11(50) PVAc-12(50) | 25 | 0.008 | 1800 | 93 | MMM | 2.0 |
| Comparative Example 1 | PVAc-13 | 25 | 0.006 | 1800 | 93 | — | — |
| Comparative Example 2 | PVAc-14(50) PVAc-15(50) | 25 | 0.008 | 1800 | 93 | MMM | 2.0 |
| Comparative Example 3 | PVAc-16(50) PVAc-17(50) | 25 | 0.008 | 1800 | 93 | MMM | 2.0 |
| Comparative Example 4 | PVAc-18(50) PVAc-19(50) | 25 | 0.008 | 1800 | 93 | MMM | 2.0 |
| Comparative Example 5 | PVAc-20 | 25 | 0.008 | 2300 | 93 | MMM | 2.0 |

|  | Value of Equation (1) ($Mw_{UV}/Mw_{RI}$) | Value of Equation (2) ($Mw_{UV}/Mn_{UV}$) | Value of Equation (3) ($A_{280}$) | PVA Dispersibility | Film Cold Water Solubility | Film Mechanical Strength |
|---|---|---|---|---|---|---|
| Example 1 | 0.95 | 3.2 | 0.18 | A | A | A |
| Example 2 | 1.03 | 3.0 | 0.15 | A | A | B |
| Example 3 | 0.96 | 3.2 | 0.01 | A | B | A |
| Example 4 | 0.95 | 3.3 | 0.03 | B | B | A |
| Example 5 | 0.95 | 3.2 | 0.70 | B | A | B |
| Example 6 | 0.95 | 3.2 | 0.02 | A | B | A |
| Example 7 | 1.15 | 3.2 | 0.18 | B | A | B |
| Example 8 | 0.85 | 3.2 | 0.18 | B | B | A |
| Example 9 | 0.95 | 7.5 | 0.18 | B | A | B |
| Comparative Example 1 | — | — | — | A | C | A |
| Comparative Example 2 | 1.25 | 3.2 | 0.18 | B | B | C |
| Comparative Example 3 | 0.75 | 3.2 | 0.18 | C | C | B |
| Comparative Example 4 | 0.95 | 8.5 | 0.18 | C | B | C |
| Comparative Example 5 | 1.23 | 3.2 | 0.18 | B | B | C |

[1] Numerical values in parentheses are PVAc mixing mass ratio.
[2] MMM: monomethyl maleate IA: itaconic acid MA: methyl acrylate As indicated in Table 2, it was found that the modified PVA of the present invention was excellent in dispersibility in water. Further, it was found that the water-soluble film of the present invention containing the modified PVA was excellent in cold water solubility and mechanical strength.

From the above results, the modified PVA of the present invention exhibiting a specific absorbance and specific molecular weight distribution is excellent in dispersibility in water. The water-soluble film containing the carboxyl group-modified PVA is excellent in cold water solubility and mechanical strength, and thus used preferably as a packaging material. The water-soluble film of the present invention is therefore useful in a wide range of fields, such as chemical packaging materials for fabric detergents, bleaches, agrochemicals and the like in liquid, powder, granules, and lamp.

The invention claimed is:
1. A modified polyvinyl alcohol obtained by copolymerizing a vinyl ester monomer with a monomer selected from the group consisting of maleic acid, a maleic acid salt, a maleic acid ester, itaconic acid, itaconic acid salt thereof, a itaconic acid ester, fumaric acid, fumaric acid salt thereof, a fumaric acid ester, maleic anhydride, a maleic anhydride derivative, itaconic anhydride or a itaconic anhydride derivative, acrylic acid, an acrylic acid salt thereof, an acrylic acid ester, methacrylic acid, methacrylic acid salt, a methacrylic acid ester, and a combination thereof; and saponifying the resultant copolymer, wherein the modified polyvinyl alcohol has a degree of saponification of from 50 to 99.99 mol % and a viscosity-average degree of polymerization of from 200 to 5000 and satisfies formulae (1) to (3) below, $$0.8 \leq (Mw_{UV}/Mw_{RI}) \leq 1.2 \quad (1)$$

$$2 \leq (Mw_{UV}/Mn_{UV}) \leq 8 \quad (2)$$

$$0.01 \leq A_{280} \leq 0.8 \quad (3)$$

Where $Mw_{UV}$ is weight-average molecular weight of the modified polyvinyl alcohol measured by an absorptiometer at a measurement wavelength of 280 nm in gel permeation chromatographic measurement, $Mw_{RI}$ is weight-average molecular weight of the modified polyvinyl alcohol measured by a differential refractive index detector in the gel permeation chromatographic measurement, $Mn_{UV}$ is number-average molecular weight of the modified polyvinyl alcohol measured by the absorptiometer at the measurement wavelength of 280 nm in the gel permeation chromatographic measurement, and $A_{280}$ is absorbance at an optical path length of 10 mm and the wavelength of 280 nm of a 1 mass % aqueous solution of the modified polyvinyl alcohol.

2. The modified polyvinyl alcohol according to claim 1, wherein a content of the monomer is from 0.1 to 10 mol %.

3. A water-soluble film, comprising:
the modified polyvinyl alcohol according to claim 2.

4. A water-soluble film, comprising:
the modified polyvinyl alcohol according to claim 1.

5. A package, comprising:
a chemical contained in the water-soluble film according to claim 4.

6. The package according to claim 3, wherein the chemical is an agrochemical or a detergent.

* * * * *

UNITED STATES PATENT AND TRADEMARK OFFICE
CERTIFICATE OF CORRECTION

PATENT NO. : 9,908,957 B2
APPLICATION NO. : 15/108174
DATED : March 6, 2018
INVENTOR(S) : Yoko Mori et al.

Page 1 of 1

It is certified that error appears in the above-identified patent and that said Letters Patent is hereby corrected as shown below:

In the Claims

Column 18, Line 17 Claim 6, "claim 3" should read --claim 5--.

Signed and Sealed this
Twenty-ninth Day of May, 2018

Andrei Iancu
*Director of the United States Patent and Trademark Office*